(12) United States Patent
Watanabe et al.

(10) Patent No.: US 10,646,851 B2
(45) Date of Patent: *May 12, 2020

(54) SEPARATION MATERIAL

(71) Applicant: Hitachi Chemical Company, LTD., Tokyo (JP)

(72) Inventors: Masaru Watanabe, Tokyo (JP); Tomoko Higashiuchi, Tokyo (JP); Fumihiko Kawauchi, Tokyo (JP); Yasushi Gotoh, Tokyo (JP); Michio Butsugan, Hitachi (JP)

(73) Assignee: HITACHI CHEMICAL COMPANY, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/544,414

(22) PCT Filed: Jan. 19, 2016

(86) PCT No.: PCT/JP2016/051473
§ 371 (c)(1),
(2) Date: Jul. 18, 2017

(87) PCT Pub. No.: WO2016/117572
PCT Pub. Date: Jul. 28, 2016

(65) Prior Publication Data
US 2017/0341058 A1 Nov. 30, 2017

(30) Foreign Application Priority Data
Jan. 19, 2015 (JP) .................................. 2015-007777

(51) Int. Cl.
*B01J 20/32* (2006.01)
*G01N 30/88* (2006.01)
(Continued)

(52) U.S. Cl.
CPC ........ *B01J 20/3282* (2013.01); *B01D 15/361* (2013.01); *B01J 20/24* (2013.01);
(Continued)

(58) Field of Classification Search
None
See application file for complete search history.

(56) References Cited

U.S. PATENT DOCUMENTS 3,966,489 A 6/1976 Barrett et al.
4,135,943 A * 1/1979 Morishita .......... B01J 20/28004
106/162.1

(Continued)

FOREIGN PATENT DOCUMENTS

EP 2545989 A1 1/2013
JP S60-169427 A 9/1985
(Continued)

OTHER PUBLICATIONS

Zhou, W. Q.; Gu, T. Y.; Su, Z. G.; Ma, G. H. Polymer 2007, 48, 1981-1988.*
(Continued)

*Primary Examiner* — Krishnan S Menon
(74) *Attorney, Agent, or Firm* — Fitch, Even, Tabin & Flannery, LLP

(57) ABSTRACT

The present invention provides a separation material comprising porous polymer particles that comprise a styrene-based monomer as a monomer unit; and a coating layer that comprises a macromolecule having hydroxyl groups and covers at least a portion of the surface of the porous polymer particles, wherein the rupture strength is 10 mN or higher.

9 Claims, 1 Drawing Sheet

(51) Int. Cl.
| | |
|---|---|
| *C08J 7/04* | (2020.01) |
| *B01J 20/24* | (2006.01) |
| *B01D 15/36* | (2006.01) |
| *B01J 20/26* | (2006.01) |
| *B01J 20/28* | (2006.01) |
| *B01J 20/285* | (2006.01) |
| *B01J 20/30* | (2006.01) |
| *B01J 41/14* | (2006.01) |
| *C07K 1/18* | (2006.01) |
| *B01J 20/281* | (2006.01) |
| *C07K 1/16* | (2006.01) |

(52) U.S. Cl.
CPC ........... *B01J 20/267* (2013.01); *B01J 20/285* (2013.01); *B01J 20/28016* (2013.01); *B01J 20/28052* (2013.01); *B01J 20/3085* (2013.01); *B01J 20/321* (2013.01); *B01J 20/3217* (2013.01); *B01J 20/3293* (2013.01); *B01J 41/14* (2013.01); *C07K 1/18* (2013.01); *C08J 7/0427* (2020.01); *G01N 30/482* (2013.01); *G01N 30/88* (2013.01); *B01J 2220/445* (2013.01); *B01J 2220/52* (2013.01); *C07K 1/16* (2013.01); *C08J 2325/02* (2013.01); *C08J 2405/12* (2013.01)

(56) References Cited

U.S. PATENT DOCUMENTS

| | | |
|---|---|---|
| 4,335,017 A | 6/1982 | Miles et al. |
| 4,336,161 A | 6/1982 | Rosevear et al. |
| 4,965,289 A | 10/1990 | Sherrington et al. |
| 5,114,577 A | 5/1992 | Kusano et al. |

FOREIGN PATENT DOCUMENTS

| | | |
|---|---|---|
| JP | S63-236539 A | 10/1988 |
| JP | H1-254247 A | 9/1998 |
| JP | 2003-093801 A | 4/2003 |
| JP | 2006-095516 A | 4/2006 |
| JP | 2007-017445 A | 1/2007 |
| JP | 2009-221428 A | 10/2009 |
| JP | 2009-244067 A | 10/2009 |
| JP | 2014-521078 A | 8/2014 |
| WO | 2006/025556 A1 | 3/2006 |

OTHER PUBLICATIONS

International Search Report for PCT/JP2016/051473 dated Mar. 22, 2016; English translation submitted herewith (5 pages).
Qu Jian-Bo et al, "A novel stationary phase derivatized from hydrophilic gigaporous polystyrene-based microspberes for high-speed protein chromatography", Journal of Chromatography A, 2009, 1216, p. 6511-p. 6516.
Qu Jian-Bo et al, "An Effective Way to Hydrophilize Gigaporous Polystyrene Microspheres as Rapid Chromatographic Separation Media for Proteins", Langmuir, 2008, 24, p. I3646-p. I3652.
International Preliminary Report on Patentability of WO Appln. No. PCT/JP2016/051473 dated Aug. 3, 2017 in English.

* cited by examiner

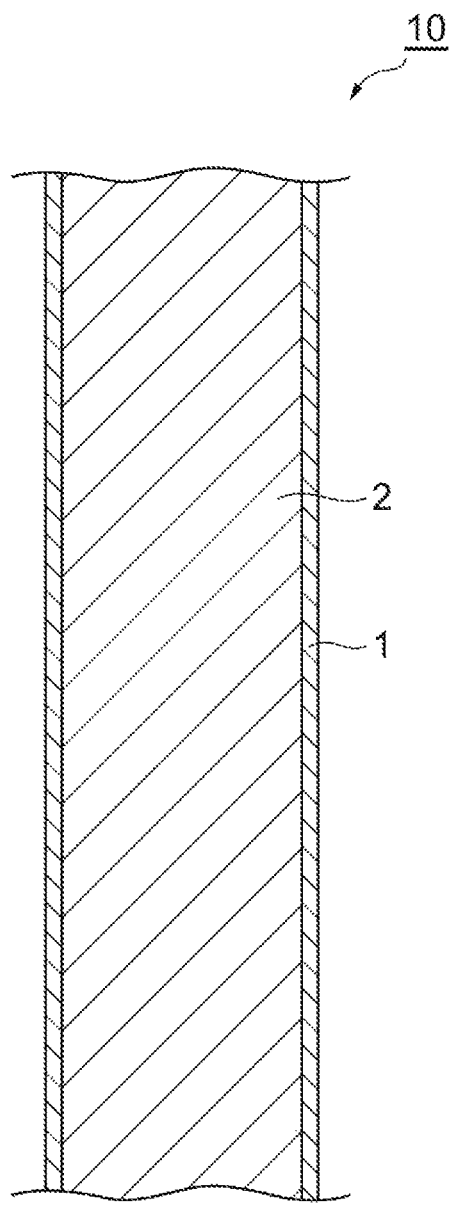

SEPARATION MATERIAL

CROSS-REFERENCE TO RELATED APPLICATIONS

This application is a U.S. national phase application filed under 35 U.S.C. § 371 of International Application PCT/JP2016/051473, filed on Jan. 19, 2016, designating the United States, which claims benefit of the filing dates of JP 2015-007777, filed Jan. 19, 2015, which is hereby incorporated herein by reference in its entirety.

TECHNICAL FIELD

The present invention relates to a separation material.

BACKGROUND ART

Conventionally, in a case in which bio-macromolecules that are represented by proteins are separated and purified, generally, porous type particles having a synthetic macromolecule as a matrix, particles having a crosslinked gel of a hydrophilic natural macromolecule as a matrix, and the like are used. An ion exchanger having the porous type synthetic macromolecule as a matrix has an advantage that the volume change caused by salt concentration is small, and in a case in which the ion exchanger is packed in a column and used for chromatography, the pressure resistance at the time of liquid permeation is favorable. However, when this ion exchanger is used for the separation of a protein or the like, non-specific adsorption such as irreversible adsorption based on hydrophobic interaction occurs, and therefore, there is a problem that asymmetrization of peaks occurs, or a protein adsorbed to an ion exchanger by the hydrophobic interaction remains adsorbed and cannot be collected.

Meanwhile, in the case of ion exchangers having crosslinked gels of hydrophilic natural macromolecules, which are represented by polysaccharides such as dextran and agarose as matrices, there is an advantage that non-specific adsorption of proteins hardly occurs. However, these ion exchangers have a defect that the ion exchangers swell conspicuously in aqueous solutions, undergo a large volume change due to the ionic strength of a solution and a large volume change between free acid type and load-sensitive type, and do not have sufficient mechanical strength. Particularly, in the case of using a crosslinked gel in chromatography, the ion exchangers have a defect that there is a high pressure loss at the time of liquid permeation, and the gel is consolidated as a result of liquid permeation.

In order to overcome the defects of crosslinked gels of hydrophilic natural macromolecules, attempts have been hitherto made to combine the crosslinked gels with rigid substances that serve as a so-called "skeleton".

For example, it is disclosed in Patent Literature 1 that when a composite in which a gel such as a natural macromolecule gel is retained within pores of a porous macromolecule is used in the field of peptide synthesis, the load factors of reactive substances can be increased, and synthesis can be achieved with high yield.

Furthermore, in Patent Literature 1, since a hard synthetic macromolecule substance is surrounded by a gel, an effect is described that even if the composite is used in the form of a column bed, there is no change in volume, and the pressure of the flow-through that permeates through the column does not change.

In Patent Literatures 2 and 3, separation materials in which a xerogel of a polysaccharide such as dextran or cellulose is retained in an inorganic porous body such as celite, are disclosed. This gel is provided with a diethylaminoethyl (DEAE) group or the like in order to add sorption performance, and the gel is used for the removal of hemoglobin. As an effect thereof, satisfactory liquid permeability in columns is mentioned.

In Patent Literature 4, an ion exchanger of a hybrid copolymer, in which pores of a copolymer having a macro network structure are filled with a crosslinked copolymer gel synthesized from monomers, is disclosed. A crosslinked copolymer gel has problems with pressure loss, volume change and the like in the case of having a low degree of crosslinking; however, it is described that by employing a hybrid copolymer, the liquid permeation characteristics are improved so that the pressure loss is decreased, and that the ion exchange capacity is increased while the leakage behavior is improved.

Compositized filler materials in which a crosslinked gel of a hydrophilic natural macromolecule having a macro network structure is filled in the pores of an organic synthetic polymer base, have been proposed (see Patent Literatures 5 and 6).

In Patent Literature 7, synthesis of porous particles formed by copolymerization of glycidyl methacrylate and an acrylic crosslinking monomer is disclosed.

CITATION LIST

Patent Literature

Patent Literature 1: U.S. Pat. No. 4,965,289
Patent Literature 2: U.S. Pat. No. 4,335,017
Patent Literature 3: U.S. Pat. No. 4,336,161
Patent Literature 4: U.S. Pat. No. 3,966,489
Patent Literature 5: JP H01-254247 A
Patent Literature 6: U.S. Pat. No. 5,114,577
Patent Literature 7: JP 2009-244067 A

SUMMARY OF INVENTION

Technical Problem

In regard to conventional column packing materials, it is difficult to address liquid permeability and durability, which are problems of natural macromolecules; and alkali resistance, reduction of non-specific adsorption, low protein adsorption amount and the like, which are problems of polymer particles, at sufficient levels.

Thus, it is an object of the present invention to provide a separation material that secures liquid permeability and durability and is capable of enhancing alkali resistance and the protein adsorption amount, and reducing non-specific adsorption.

Solution to Problem

The present invention provides a separation material described in the following [1] to [11].

[1] A separation material comprising porous polymer particles that comprise a styrene-based monomer as a monomer unit; and a coating layer that comprises a macromolecule having hydroxyl groups and covers at least a portion of the surface of the porous polymer particles, wherein the rupture strength is 10 mN or higher.

[2] The separation material according to [1], wherein the porosity is 40% to 70%.

[3] The separation material according to [1] or [2], wherein the degree of hygroscopicity is 1% to 30% by mass.

[4] The separation material according to any one of [1] to [3], wherein the specific surface area is 30 m$^2$/g or more.

[5] The separation material according to any one of [1] to [4], wherein the porous polymer particles comprise divinylbenzene as a monomer unit at a proportion of 50% by mass or more based on the total mass of the monomers.

[6] The separation material according to any one of [1] to [5], wherein the coefficient of variation of the particle size of the porous polymer particles is 3% to 15%.

[7] The separation material according to any one of [1] to [6], wherein the macromolecule having hydroxyl groups is a polysaccharide or a modification product thereof.

[8] The separation material according to any one of [1] to [6], wherein the macromolecule having hydroxyl groups is agarose or a modification product thereof.

[9] The separation material according to any one of [1] to [8], wherein the macromolecule having hydroxyl groups is crosslinked.

[10] The separation material according to any one of [1] to [9], wherein the separation material comprises 30 to 400 mg of the coating layer per 1 g of the porous polymer particles.

[11] The separation material according to any one of [1] to [10], wherein in the case of being packed in a column, the liquid permeation rate is 800 cm/h or higher at the time when the column pressure is 0.3 MPa.

[12] A separatory column comprising a column; and the separation material according to any one of [1] to [11] that is packed in the column.

Advantageous Effects of Invention

According to the present invention, a separation material that secures liquid permeability and durability, and is capable of enhancing alkali resistance, pressure resistance and the protein adsorption amount, and reducing non-specific adsorption, can be provided.

BRIEF DESCRIPTION OF DRAWINGS

FIG. 1 is a cross-sectional view illustrating an embodiment of a separatory column.

DESCRIPTION OF EMBODIMENTS

Hereinafter, suitable embodiments of the present invention will be described; however, the present invention is not intended to be limited to these embodiments.

<Separation Material>

The separation material of the present embodiment comprises porous polymer particles; and a coating layer that covers at least a portion of the surface of the porous polymer particles. In the present specification, the "surface of the porous polymer particles" is meant to include not only the external surface of the porous polymer particles, but also the surface of pores in the interior of the porous polymer particles.

(Porous Polymer Particles)

The porous polymer particles of the present embodiment are particles obtained by curing a monomer including a porosifier, and can be synthesized by, for example, conventional suspension polymerization and emulsion polymerization. There are no particular limitations on the monomer, and for example, a styrene-based monomer can be used. Specific examples of the monomer include polyfunctional monomers and monofunctional monomers such as follows.

Examples of the polyfunctional monomers include divinyl compounds such as divinylbenzene, divinylbiphenyl, divinylnaphthalene, and divinylphenanthrene. These polyfunctional monomers can be used singly, or in combination of two or more kinds thereof. Among the above-described monomers, from the viewpoint of having excellent durability, acid resistance and alkali resistance, it is preferable to use divinylbenzene.

In a case in which the porous polymer particles comprise divinylbenzene as a monomer unit, it is preferable that the polymer particles comprise divinylbenzene at a proportion of 50% by mass or more, more preferably at a proportion of 60% by mass or more, and even more preferably at a proportion of 70% by mass or more, based on the total mass of the monomers. When the porous polymer particles comprise divinylbenzene at a proportion of 50% by mass or more based on the total mass of the monomers, the porous polymer particles tend to have excellent alkali resistance and pressure resistance.

Examples of the monofunctional monomers include styrene and derivatives thereof, such as styrene, o-methylstyrene, m-methylstyrene, p-methylstyrene, α-methylstyrene, o-ethylstyrene, m-ethylstyrene, p-ethylstyrene, 2,4-dimethylstyrene, p-n-butylstyrene, p-t-butylstyrene, p-n-hexylstyrene, p-n-octylstyrene, p-n-nonylstyrene, p-n-decylstyrene, p-n-dodecylstyrene, p-methoxystyrene, p-phenylstyrene, p-chlorostyrene, and 3,4-dichlorostyrene. These monofunctional monomers can be used singly or in combination of two or more kinds thereof. Among these, from the viewpoint of obtaining excellent acid resistance and alkali resistance, it is preferable to use styrene. Furthermore, styrene derivatives having functional groups such as a carboxyl group, an amino group, a hydroxyl group and an aldehyde group, can also be used.

Examples of the porosifier include aliphatic or aromatic hydrocarbons, esters, ketones, ethers, and alcohols, which are organic solvents that accelerate phase separation at the time of polymerization and accelerate porosification of particles. Specific examples include toluene, xylene, cyclohexane, octane, butyl acetate, dibutyl phthalate, methyl ethyl ketone, dibutyl ether, 1-hexanol, 2-octanol, decanol, lauryl alcohol, and cyclohexanol. These porosifiers can be used singly or in combination of two or more kinds thereof.

The porosifier can be used in an amount of 0% to 200% by mass with respect to the total mass of the monomers. Porosity of the porous polymer particles can be controlled by the amount of the porosifier. Furthermore, the size and shape of the pores of the porous polymer particles can be controlled by the type of the porosifier.

Water that is used as a solvent can also be used as the porosifier. In a case in which water is used as the porosifier, porosification can be achieved by dissolving an oil-soluble surfactant in the monomer, and absorbing water.

Examples of the oil-soluble surfactant that is used for porosification include a sorbitan monoester of a branched C16-C24 fatty acid, a linear unsaturated C16-C22 fatty acid or a chain-like saturated C12-C14 fatty acid, for example, sorbitan monolaurate, sorbitan monooleate, sorbitan monomyristate, or a sorbitan monoester derived from coconut fatty acids; a diglycerol monoester of a branched C16-C24 fatty acid, a linear unsaturated C16-C22 fatty acid, or a linear saturated C12-C14 fatty acid, for example, diglycerol monooleate (for example, a diglycerol monoester of a C18:1 (number of carbon atoms: 18, number of double bonds: 1) fatty acid), diglycerol monomyristate, diglycerol monoisostearate, or diglycerol monoester of coconut fatty acids; a diglycerol monoaliphatic ether of a branched C16-C24 alcohol (for example, Guerbet alcohol), a linear unsaturated C16-C22 alcohol, or a linear saturated C12-C14 alcohol (for example, coconut fatty alcohol); and mixtures of these.

Among these, sorbitan monolaurate (for example, SPAN (registered trademark) 20; sorbitan monolaurate preferably having a purity of higher than about 40%, more preferably a purity of higher than about 50%, and most preferably a purity of higher than about 70%); sorbitan monooleate (for example, SPAN (registered trademark) 80; sobitan monooleate preferably having a purity of higher than about 40%, more preferably a purity of about 50%, and most preferably a purity of higher than about 70%); diglycerol monooleate (for example, diglycerol monooleate preferably having a purity of higher than about 40%, more preferably a purity of higher than about 50%, and most preferably a purity of higher than about 70%); diglycerol monoisostearate (for example, diglycerol monoisostearate preferably having a purity of higher than about 40%, more preferably a purity of higher than about 50%, and most preferably a purity of higher than about 70%); diglycerol monomyristate (sorbitan monomyristate preferably having a purity of higher than about 40%, more preferably a purity of higher than about 50%, and most preferably a purity of higher than about 70%); cocoyl (for example, a lauryl group or a myristoyl group) ether of diglycerol; and mixtures of these, are preferred.

It is preferable to use these oil-soluble surfactants in an amount in the range of 5% to 80% by mass with respect to the total mass of the monomers. When the content of the oil-soluble surfactant is 5% by mass or more, since stability of water droplets becomes sufficient, it is easier for large single holes to be formed. Furthermore, when the content of the oil-soluble surfactant is 80% by mass or less, it is easier for the porous polymer particles to maintain the shape after polymerization.

Examples of an aqueous medium that is used for the polymerization reaction include water, and a mixed medium of water and a water-soluble solvent (for example, a lower alcohol). The aqueous medium may include a surfactant. As the surfactant, among anionic, cationic, nonionic and zwitterionic surfactants, all can be used.

Examples of anionic surfactants include fatty acid oils such as sodium oleate and castor oil potassium; alkyl sulfuric acid ester salts such as sodium lauryl sulfate and ammonium lauryl sulfate; alkyl benzenesulfonic acid salts such as sodium dodecyl benzenesulfonate; alkyl naphthalenesulfonic acid salts; alkanesulfonic acid salts; dialkyl sulfosuccinic acid salts such as sodium dioctyl sulfosuccinate; alkenyl succinic acid salts (dipotassium salts); alkyl phosphoric acid ester salts; naphthalenesulfonic acid-formalin condensate, polyoxyethylene alkyl phenyl ether sulfuric acid ester salts; polyoxyethylene alkyl ether sulfuric acid salts such as sodium polyoxyethylene lauryl ether sulfate; and polyoxyethylene alkyl sulfuric acid ester salts.

Examples of cationic surfactants include alkyl amine salts such as lauryl amine acetate and stearyl amine acetate; and quaternary ammonium salts such as lauryl trimethylammonium chloride.

Examples of nonionic surfactants include hydrocarbon-based nonionic surfactants such as polyethylene glycol alkyl ethers, polyethylene glycol alkyl aryl ethers, polyethylene glycol esters, polyethylene glycol sorbitan esters, and polyalkylene glycol alkyl amines or amides; polyether-modified silicone-based nonionic surfactants such as polyethylene oxide adducts and polypropylene oxide adducts of silicones; and fluorine-based nonionic surfactants such as perfluoroalkyl glycols.

Examples of zwitterionic surfactants include hydrocarbon surfactants such as lauryl dimethylamine oxide; phosphoric acid ester-based surfactants, and phosphorous acid ester-based surfactants.

The surfactants may be used singly or in combination of two or more kinds thereof. Among the surfactants described above, from the viewpoint of dispersion stability at the time of monomer polymerization, anionic surfactants are preferred.

As a polymerization initiator that is added as necessary, for example, organic peroxides such as benzoyl peroxide, lauroyl peroxide, benzoyl orthochloroperoxide, benzoyl orthomethoxyperoxide, 3,5,5-trimethylhexanoyl peroxide, tert-butyl peroxy-2-ethylhexanoate, and di-tert-butyl peroxide; azo-based compounds such as 2,2'-azobisisobutyronitrile, 1,1'-azobiscyclohexanecarbonitrile, and 2,2'-azobis(2,4-dimethylvaleronitrile). The polymerization initiator can be used in an amount in the range of 0.1 to 7.0 parts by mass with respect to 100 parts by mass of the monomers.

The polymerization temperature can be appropriately selected according to the types of the monomer and the polymerization initiator. The polymerization temperature is preferably 25° to 110° C., and more preferably 50° C. to 100° C.

In regard to the synthesis of porous polymer particles, in order to enhance dispersion stability of the particles, a macromolecule dispersion stabilizer may also be used.

Examples of the macromolecule dispersion stabilizer include polyvinyl alcohol, polycarboxylic acids, celluloses (hydroxyethyl cellulose, carboxymethyl cellulose, methyl cellulose, and the like), and polyvinylpyrrolidone, and inorganic water-soluble macromolecule compounds such as sodium tripolyphosphate can also be used in combination. Among these, polyvinyl alcohol or polyvinylpyrrolidone is preferred. The amount of addition of the macromolecule dispersion stabilizer is preferably 1 to 10 parts by mass with respect to 100 parts by mass of the monomers.

In order to prevent the monomers from being polymerized alone, water-soluble polymerization inhibitors such as nitrous acid salts, sulfurous acid salts, hydroquinones, ascorbic acids, water-soluble vitamins B compounds, citric acid, and polyphenols may also be used.

The average particle size of the porous polymer particles is preferably 300 μm or less, more preferably 150 μm or less, and even more preferably 100 μm or less. Furthermore, the average particle size of the porous polymer particles is preferably 10 μm or more, more preferably 30 μm or more, and even more preferably 50 μm or more, from the viewpoint of enhancing liquid permeability.

The coefficient of variation (C.V.) of the particle size of the porous polymer particles is preferably 3% to 15%, more preferably 5% to 15%, and even more preferably 5% to 10%, from the viewpoint of enhancing liquid permeability. As a method for reducing the C.V., a method of monodispersing the porous polymer particles by means of an emulsifying apparatus such as a MICRO PROCESS SERVER (manufactured by Hitachi, Ltd.) may be used.

The average particle size and the C.V. (coefficient of variation) of the particle size of the porous polymer particles or the separation material can be determined by the following measurement method.

1) Particles are dispersed in water (including a dispersant such as a surfactant) using an ultrasonic dispersing apparatus, and thus a dispersion liquid including 1% by mass of porous polymer particles is prepared.

2) The average particle size and the C.V. (coefficient of variation) of the particle size are measured from the images of about 10,000 particles in the dispersion liquid, using a particle size distribution meter (SYSMEX FLOW, manufactured by Sysmex Corp.).

The pore volume (porosity) of the porous polymer particles is preferably from 30% by volume to 70% by volume, and more preferably from 40% by volume to 70% by volume, based on the total volume (including the pore volume) of the porous polymer particles. It is preferable that the porous polymer particles have pores having a pore size of 0.1 µm or more and less than 0.5 µm, that is, macropores (macrovoids). The mode diameter in the pore size distribution (most frequent value of the pore size distribution, maximum frequency pore size, average pore size) of the porous polymer particles is preferably 0.1 µm or more and less than 0.5 µm, and more preferably 0.2 µm or more and less than 0.5 µm. When the mode diameter in the pore size distribution is 0.1 µm or more, there is a tendency that substances can easily enter into the pores, and when the mode diameter in the pore size distribution is less than 0.5 µm, the specific surface area becomes sufficient. These can be adjusted by means of the porosifier mentioned above.

The specific surface area of the porous polymer particles is preferably 30 m$^2$/g or more. From the viewpoint of higher practical usability, the specific surface area is more preferably 35 m$^2$/g or more, and even more preferably 40 m$^2$/g or more. When the specific surface area is 30 m$^2$/g or more, the adsorption amount of the substance to be separated tends to increase. The upper limit of the specific surface area of the porous polymer particles is not particularly limited; however, for example, the specific surface area can be adjusted to be 200 m$^2$/g or less and 100 m$^2$/g or less.

(Coating Layer)

The coating layer of the present embodiment comprises a macromolecule having hydroxyl groups. When the porous polymer particles are coated with a macromolecule having hydroxyl groups, increase in the column pressure can be suppressed, non-specific adsorption of proteins can also be suppressed, and the protein adsorption amount of the separation material tends to improve. Furthermore, when the macromolecule having hydroxyl groups is crosslinked, the increase in the column pressure can be further suppressed.

(Macromolecule Having Hydroxyl Groups)

It is preferable that the macromolecule having hydroxyl groups has two or more hydroxyl groups in one molecule, and it is more preferable that the macromolecule having hydroxyl groups is a hydrophilic macromolecule. Examples of the macromolecule having hydroxyl groups include polysaccharides and polyvinyl alcohol. Preferred examples of the polysaccharides include agarose, dextran, cellulose, and chitosan. As the macromolecule having hydroxyl groups, for example, a macromolecule having a weight average molecular weight of about 10,000 to 200,000 can be used.

It is preferable that the macromolecule having hydroxyl groups is a modification product that has been modified with a hydrophobic group, from the viewpoint of enhancing the interface adsorption capacity. Examples of the hydrophobic group include an alkyl group having 1 to 6 carbon atoms, and an aryl group having 6 to 10 carbon atoms. Examples of the alkyl group having 1 to 6 carbon atoms include a methyl group, an ethyl group, and a propyl group. Examples of the aryl group having 6 to 10 carbon atoms include a phenyl group and a naphthyl group. A hydrophobic group can be introduced by causing a compound that has a functional group which reacts with a hydroxyl group (for example, an epoxy group) and has a hydrophobic group (for example, glycidyl phenyl ether), to react with the macromolecule having hydroxyl groups by a conventionally known method.

(Method for Forming Coating Layer)

The coating layer that comprises a macromolecule having hydroxyl groups can be formed by, for example, a method disclosed below.

First, a solution of a macromolecule having hydroxyl groups is adsorbed onto the surface of porous polymer particles. The solvent for the solution of a macromolecule having hydroxyl groups is not particularly limited as long as the solvent can dissolve the macromolecule having hydroxyl groups; however, water is most general. The concentration of the macromolecule that is dissolved in the solvent is preferably 5 to 20 (mg/mL).

This solution is impregnated into the porous polymer particles. Regarding the method for impregnation, the porous polymer particles are added to the solution of a macromolecule having hydroxyl groups, and the solution is left to stand for a certain time. The impregnation time may vary depending on the surface state of the porous body; however, usually, when impregnation is carried out for one day and one night, the macromolecule concentration in the interior of the porous body reaches an equilibrium state with the external concentration. Subsequently, the porous body is washed with a solvent such as water or an alcohol, and any unadsorbed portion of the macromolecule having hydroxyl groups is removed.

(Crosslinking Treatment)

Next, a crosslinking agent is added thereto, and the macromolecule having hydroxyl groups that has adsorbed onto the surface of the porous polymer particles is subjected to a crosslinking reaction. Thus, a crosslinked product is formed. At this time, the crosslinked product has a three-dimensionally crosslinked network structure having hydroxyl groups.

Examples of the crosslinking agent include compounds each having two or more functional groups that are active on a hydroxyl group, such as epihalohydrins such as epichlorohydrin; dialdehyde compounds such as glutaraldehyde; diisocyanate compounds such as methylene diisocyanate; and glycidyl compounds such as ethylene glycol diglycidyl ether. Furthermore, in a case in which a compound having amino groups, such as chitosan, is used as the macromolecule having hydroxyl groups, a dihalide such as dichlorooctane can also be used as the crosslinking agent.

For this crosslinking reaction, a catalyst is usually used. Regarding the catalyst, a conventionally known catalyst can be used as appropriate in accordance with the type of the crosslinking agent; however, for example, in a case in which the crosslinking agent is epichlorohydrin, an alkali such as sodium hydroxide is effective, and in the case of a dialdehyde compound, a mineral acid such as hydrochloric acid is effective.

The crosslinking reaction by a crosslinking agent is usually carried out by adding a crosslinking agent to a system in which the separation material has been dispersed and suspended in an appropriate medium. Regarding the amount of addition of the crosslinking agent, in a case in which a polysaccharide is used as the macromolecule having hydroxyl groups, when one unit of a monosaccharide is regarded as one mole, the amount of addition can be selected according to the performance of the separation material, for example, within the range of 0.1 to 100 times the molar amount of the monosaccharide. Generally, when the amount of addition of the crosslinking agent is reduced, there is a tendency that the coating layer is easily detached from the porous polymer particles. Furthermore, in a case in which the amount of addition of the crosslinking agent is in excess, and the reaction ratio with the macromolecule having hydroxyl groups is high, the characteristics of the macromolecule having hydroxyl groups as a raw material tend to be impaired.

The amount of use of the catalyst may vary with the type of the crosslinking agent; however, usually in a case in which a polysaccharide is used as the macromolecule having hydroxyl groups, when one unit of the monosaccharide that forms the polysaccharide is regarded as one mole, the catalyst is used preferably in an amount in the range of 0.01 to 10 times, and more preferably 0.1 to 5 times, the molar amount of this monosaccharide.

For example, when temperature conditions are employed as the crosslinking reaction conditions, when the temperature of the reaction system is raised, and the temperature reaches the reaction temperature, a crosslinking reaction occurs.

Regarding the medium in which the porous polymer particles that have been impregnated with a solution of a macromolecule having hydroxyl groups are dispersed and suspended, it is necessary that the medium does not extract a macromolecule, a crosslinking agent and the like from the macromolecule solution that has been impregnated, and is inactive to the crosslinking reaction. Specific examples of the medium include water and an alcohol.

The crosslinking reaction is usually carried out at a temperature in the range of 5° C. to 90° C. for 1 to 10 hours. Preferably, the reaction is carried out at a temperature in the range of 30° C. to 90° C.

After completion of the crosslinking reaction, when the particles thus produced are separated by filtration and then washed with water or a hydrophilic organic solvent such as methanol or ethanol, and any unreacted macromolecule, the medium for suspending, and the like are removed, a separation material in which at least a portion of the surface of porous polymer particles is covered by a coating layer comprising a macromolecule having hydroxyl groups is able to be obtained. It is preferable that the separation material of the present embodiment comprises 30 to 400 mg of the coating layer per 1 g of the porous polymer particles. The amount of the coating layer can be measured from weight reduction after thermal decomposition, or the like.

(Introduction of Ion Exchanging Group)

The separation material that comprises a coating layer can be used for ion exchange purification, affinity purification and the like, by introducing an ion exchanging group, a ligand (Protein A) or the like via a hydroxyl group or the like on the surface. As a method for introducing an ion exchanging group, for example, a method of using a halogenated alkyl compound may be mentioned.

Examples of the halogenated alkyl compound include a monohalogenocarboxylic acid such as a monohalogenoacetic acid or a monohalogenopropionic acid, and a sodium salt thereof; a primary, secondary or tertiary amine having at least one halogenated alkyl group, such as diethylaminoethyl chloride; and hydrochloride of a quaternary ammonium having a halogenated alkyl group. These halogenated alkyl compounds are preferably bromides or chlorides. The amount of use of the halogenated alkyl compound is preferably 0.2% by mass or more with respect to the total mass of the separation material to which an ion exchanging group is imparted.

For the introduction of an ion exchanging group, it is effective to use an organic solvent in order to accelerate the reaction. Examples of the organic solvent include alcohols such as ethanol, 1-propanol, 2-propanol, 1-butanol, isobutanol, 1-pentanol, and isopentanol.

Since the introduction of an ion exchanging group is usually carried out into a hydroxyl group on the separation material surface, particles in a wet state are dehydrated by filtration or the like, and then the particles are immersed in an alkaline aqueous solution at a predetermined concentration and are left to stand for a certain time. Subsequently, the halogenated alkyl compound is added and reacted in a water-organic solvent mixed system. It is preferable that this reaction is performed at a temperature of 40° C. to 90° C. for 0.5 to 12 hours. The ion exchanging group to be provided is determined based on the type of the halogenated alkyl compound used for the above-described reaction.

As a method for introducing an amino group, which is a weakly basic group, as the ion exchanging group, a method of reacting, among the above-mentioned halogenated alkyl compounds, a mono-, di- or trialkylamine, a mono-, di- or trialkanolamine, a mono-alkyl-mono-alkanolamine, a di-alkyl-mono-alkanolamine, a mono-alkyl-di-alkanolamine, or the like, all of which have at least one alkyl group in which some of hydrogen atoms have been substituted by chlorine atoms, may be mentioned. The amount of use of these halogenated alkyl compounds is preferably 0.2% by mass or more with respect to the total mass of the separation material. The reaction conditions are preferably 40° C. to 90° C. and 0.5 to 12 hours.

As a method for introducing a quaternary ammonium group, which is a strongly basic group, as the ion exchanging group, a method of first introducing a tertiary amino group, reacting the tertiary amino group with a halogenated alkyl compound such as epichlorohydrin, and converting the tertiary amino group into a quaternary ammonium group, may be mentioned. Furthermore, hydrochloride of a quaternary ammonium or the like may also be reacted with the separation material.

As a method for introducing a carboxyl group, which is a weakly acidic group, as the ion exchanging group, a method of reacting a monohalogenocarboxylic acid such as a monohalogenoacetic acid or a monohalogenopropionic acid, or a sodium salt thereof as the halogenated alkyl compound, may be mentioned. The amount of use of these halogenated alkyl compounds is preferably 0.2% by mass or more with respect to the total mass of the separation material into which the ion exchanging group is introduced.

As a method for introducing a sulfonic acid group, which is a strongly acidic group, as the ion exchanging group, a method of reacting the separation material with a glycidyl compound such as epichlorohydrin, and adding the separation material to a saturated aqueous solution of a sulfurous acid salt or a bisulfurous acid salt, such as sodium sulfite or sodium bisulfite, may be mentioned. The reaction conditions are preferably 30° C. to 90° C. and 1 to 10 hours.

Meanwhile, as a method for introducing an ion exchanging group, a method of reacting the separation material with 1,3-propanesultone in an alkaline atmosphere may also be mentioned. It is preferable to use 1,3-propanesultone in an amount of 0.4% by mass or more with respect to the total mass of the separation material. The reaction conditions are preferably 0° C. to 90° C. and 0.5 to 12 hours.

The degree of hygroscopicity of the separation material of the present embodiment is measured by the following method. 1 g of a dry separation material is left to stand for 18 hours in a constant temperature constant humidity test chamber (temperature 60° C., humidity 90%), and then the mass of the separation material is measured again. Thereby, the degree of hygroscopicity is calculated by the following formula.

(Separation material mass after moisture absorption−1) g/1 g×100=Degree of hygroscopicity (%)

The degree of hygroscopicity of the separation material of the present embodiment is preferably 1% to 30% by mass, more preferably 1% to 20% by mass, and even more preferably 1% to 10% by mass. When the degree of hygroscopicity of the separation material is 30% by mass or less, the decrease in liquid permeability of the separation material due to the thickness of the coating layer can be suppressed.

The average pore size, the mode diameter in the pore size distribution, the specific surface area, and the porosity of the separation material or porous polymer particles of the present embodiment are values measured with a mercury intrusion analyzer (AUTOPORE; manufactured by Shimadzu Corp.), and these are measured as follows. 0.05 g of a sample is added to a standard 5-mL cell for powder (stem volume 0.4 mL), and measurement is made under the conditions of an initial pressure of 21 kPa (about 3 psia, equivalent to a pore diameter of about 60 μm). The mercury parameter is set to have a mercury contact angle of 130 degrees, which is an apparatus default value, and a mercury surface tension of 485 dynes/cm. Furthermore, the respective values are calculated with limiting the pore size to the range of 0.1 to 3 μm.

The mode diameter in the pore size distribution (most frequent value of the pore size distribution, maximum frequency pore size, average pore size) of the separation material of the present embodiment is preferably 0.05 to 0.5 μm, and more preferably 0.1 to 0.5 μm. When the pore size is in these ranges, a liquid can flow easily within the particles, and the dynamic adsorption amount is likely to become large.

The specific surface area of the separation material of the present embodiment is preferably 30 m$^2$/g or more. From the viewpoint of higher practical usability, the specific surface area is more preferably 35 m$^2$/g or more, and even more preferably 40 m$^2$/g or more. When the specific surface is 30 m$^2$/g or more, the adsorption amount of the substance to be separated tends to become large. The upper limit of the specific surface area of the separation material is not particularly limited; however, the specific surface area can be adjusted to, for example, 300 m$^2$/g or less.

The porosity (pore volume) of the separation material of the present embodiment is preferably 40 to 70% by volume based on the total volume (including the pore volume) of the separation material. When the porosity is in this range, the protein adsorption amount can be made large.

The separation material of the present embodiment is suitable for the use in separation of a protein by electrostatic interaction and affinity purification. For example, when the separation material of the present embodiment is added to a mixed solution including a protein, only the protein is adsorbed onto the separation material by electrostatic interaction, and then the separation material is separated by filtration from the solution and is added to an aqueous solution having a high salt concentration, the protein that has adsorbed to the separation material can be easily released and collected. Furthermore, the separation material of the present embodiment can also be used for column chromatography. An embodiment of a separatory column is illustrated in FIG. 1. The separatory column 10 comprises a column 1 and a separation material 2 packed in the column 1.

As a bio-macromolecule that can be separated by using the separation material of the present embodiment, a water-soluble substance is preferred. Specific examples include proteins, such as blood proteins such as serum albumin and immunoglobulin; enzymes present in the living body; protein physiologically active substances produced by biotechnologies; and bio-macromolecules such as DNA and physiologically active peptides. The weight average molecular weight is preferably 2,000,000 or less, and more preferably 500,000 or less. Furthermore, it is necessary to select, according to known methods, the properties of the separation material, conditions and the like based on the isoelectric point, ionization state and the like of the protein. As the known methods, for example, the method described in JP S60-169427 A may be mentioned.

The separation material of the present embodiment has the respective advantages of particles formed from a natural macromolecule or particles formed from a synthetic macromolecule in connection with the separation of a bio-macromolecule such as a protein, by subjecting the coating layer on the porous polymer particles to a crosslinking treatment, and then introducing an ion exchanging group, Protein A or the like into the surface of the separation material. Particularly, since the porous polymer particles in the separation material of the present embodiment are particles that are obtained by the method described above, the porous polymer particles have durability and alkali resistance. Furthermore, the separation material of the present embodiment has a tendency that non-specific adsorption of proteins is reduced, and adsorption and desorption of proteins easily occurs. Furthermore, the separation material of the present embodiment has a tendency that the adsorption amount of a protein or the like under the same flow rate (dynamic adsorption amount) is large.

The liquid permeation rate according to the present embodiment represents the liquid permeation rate at the time when the separation material of the present embodiment is packed in a stainless steel column having a size of φ 7.8×300 mm, and a liquid is passed therethrough. In a case in which the separation material of the present embodiment is packed in a column, it is preferable that when the column pressure is 0.3 MPa, the liquid permeation rate is 800 cm/h or higher. In a case in which separation of a protein is performed by column chromatography, the liquid permeation rate of a protein solution or the like is generally in the range of 400 cm/h or less; however, in a case in which the separation material of the present embodiment is used, the separation material can be used at a liquid permeation rate of 800 cm/h or higher, which is faster than those of conventional separation materials for protein separation.

The average particle size of the separation material of the present embodiment is preferably 10 to 300 μm. For the use in preparative or industrial chromatography, in order to avoid an extreme increase in the column internal pressure, the average particle size is preferably 10 to 100 μm.

In a case in which the separation material of the present embodiment is used as a column packing material in column chromatography, since there is hardly any volume change within the column independently of the properties of the eluent used, operability is excellent.

The rupture strength of the separation material of the present embodiment can be calculated as follows.

The load and compression displacement at the time when particles are compressed up to 50 mN by means of a smooth cross-section (50 μm×50 μm) of a quadrangular prism at a load loading rate of 1 mN/sec under the conditions of room temperature, by using a microcompression testing machine (manufactured by Fisher Scientific Co., LLC). The load at a point at which the displacement amount changes to the largest extent during measurement is designated as the rupture strength (mN).

The rupture strength of the separation material of the present embodiment is 10 mN or greater, and preferably 15 mN or greater, from the viewpoint of having excellent durability. The upper limit of the rupture strength of the separation material is not particularly limited; however, for example, the upper limit can be set to 500 mN or less.

The rupture strength, the average pore size, the mode diameter in the pore size distribution, the specific surface area and the like of the separation material can be adjusted by appropriately selecting the ingredients of the porous polymer particles, the porosifier, the macromolecule having hydroxyl groups, and the like.

In the present embodiment, a separation material in the form of having an ion exchanging group introduced thereinto has been explained; however, even if an ion exchanging group is not introduced, the separation material can be used as a separation material. Such a separation material can be utilized in, for example, gel permeation chromatography. That is, a separatory column of the present embodiment comprises a column and the separation material of the present embodiment packed in the column.

EXAMPLES

Hereinafter, the present invention will be described by way of Examples; however, the present invention is not intended to be limited to these Examples.

Example 1

<Synthesis of Porous Polymer Particles 1>

16 g of divinylbenzene (DVB960, manufactured by Nippon Steel & Sumikin Chemical Co., Ltd.) having a purity of 96%, 6 g of SPAN 80, and 0.64 g of benzoyl peroxide were introduced into a 500-mL three-necked flask, and an aqueous solution of polyvinyl alcohol (0.5% by mass) was prepared. This aqueous solution was emulsified by using a MICRO PROCESS SERVER, subsequently the emulsion liquid thus obtained was transferred into a flask, and the emulsion liquid was stirred for about 8 hours by using a stirrer, while being heated in a water bath at 80° C. The particles thus obtained were filtered, and then washed with acetone. Thus, porous polymer particles 1 were obtained. The particle size of the particles thus obtained was measured with a flow type particle size analyzer, and the average particle size and the C.V. value of the particle size were calculated. The results are presented in Table 1.

<Formation and Crosslinking of Coating Layer>

4 g of sodium hydroxide and 0.4 g of glycidyl phenyl ether were added to 100 mL of an aqueous solution of agarose (2% by mass), and the mixture was reacted for 12 hours at 70° C. Thus, phenyl groups were introduced into agarose. The modified agarose thus obtained was reprecipitated three times with isopropyl alcohol, and was washed.

The porous polymer particles 1 were introduced into a 20 mg/mL aqueous solution of the modified agarose at a proportion of 10 g of the porous polymer particles in 700 mL of the aqueous solution, and the mixture was stirred for 24 hours at 55° C. Thereby, the modified agarose was adsorbed onto the porous polymer particles 1. After adsorption, the porous polymer particles were filtered and washed with hot water. The adsorption amount (coating amount) of the modified agarose was calculated by measuring the thermal weight reduction of the particles that had been dried. The results are presented in Table 2.

The agarose adsorbed onto the particles was crosslinked as follows. 39 g of ethylene glycol diglycidyl ether was added to a 0.4 M aqueous solution of sodium hydroxide in which 10 g of the particles were dispersed, and the mixture was stirred for 24 hours at 30° C. Subsequently, the particles were washed with a heated 2 mass % aqueous solution of sodium dodecyl sulfate, and then were washed with pure water. Thus, a separation material was obtained. The separation material was stored in water.

(Evaluation of Non-Specific Adsorption Ability for Protein)

0.5 g of the separation material thus obtained was introduced into 50 mL of a phosphate buffer solution (pH 7.4) at a BSA (Bovine Serum Albumin) concentration of 20 mg/mL, and the solution was stirred at room temperature for 24 hours. Subsequently, a supernatant was collected by centrifugation, the BSA concentration of the filtrate was measured with a spectrophotometer, and thus the amount of BSA adsorbed to the separation material was calculated as the non-specific adsorption amount. The concentration of BSA was checked from the absorbance of light at 280 nm by means of a spectrophotometer. The results are presented in Table 3.

<Introduction of Ion Exchanging Group>

Water was removed by centrifugation from the separation material dispersion liquid thus obtained, and then 20 g of the separation material was dispersed in 100 mL of an aqueous solution obtained by dissolving a predetermined amount of diethylaminoethyl chloride hydrochloride. The mixture was stirred for 10 minutes at 70° C. Subsequently, 100 mL of a 5 M aqueous solution of NaOH that had been heated to 70° C. was added thereto, and the mixture was caused to react for 1 hour. After completion of the reaction, the separation material was filtered and washed two times with water/ethanol (volume ratio 8/2), and thus a DEAE-modified separation material having a diethylaminoethyl (DEAE) group as an ion exchanging group was obtained. The mode diameter in the pore size distribution, specific surface area, and porosity of the DEAE-modified separation material thus obtained were measured by a mercury intrusion method. Rupture strength was measured by a microcompression test. The results are presented in Table 2.

The ion exchange capacity of the DEAE-modified separation material was measured as follows. The separation material in a volume of 5 mL was immersed in 20 mL of a 0.1 N aqueous solution of sodium hydroxide for 1 hour, and the mixture was stirred at room temperature. Subsequently, the separation material was washed until the pH of the water used as a washing liquid reached 7 or lower. The separation material thus washed was immersed in 20 mL of 0.1 N hydrochoric acid, and the mixture was stirred for 1 hour. The separation material was removed by filtration, and then the aqueous solution of hydrochloric acid of the filtrate was titrated to neutralization. Thereby, the ion exchange capacity of the separation material was measured. The results are presented in Table 2.

(Evaluation of Column Characteristics)

The DEAE-modified separation material thus obtained was packed in a stainless steel column having a size of φ 7.8×300 mm as a slurry (solvent: methanol) having a concentration of 30% by mass over 15 minutes. Subsequently, water was caused to flow through the column while the flow rate was varied, and the relation between the flow rate and the column pressure was measured. Thus, the liquid permeation rate (linear flow rate) at 0.3 MPa was measured. The results are presented in Table 2.

The dynamic adsorption amount was measured as follows. A 20 mmol/L Tris-hydrochloric acid buffer solution (pH 8.0) was caused to flow through a column in an amount of 10 column volumes. Subsequently, a 20 mmol/L Tris-hydrochloric acid buffer solution having a BSA concentration of 2 mg/mL was caused to flow, and the BSA concentration at the column outlet was measured by means of UV. The buffer solution was caused to flow until the BSA concentration at the column inlet coincided with the BSA concentration at the column outlet, and dilution was performed with a 1 M NaCl Tris-hydrochloric acid buffer solution in an amount of 5 column volumes. The dynamic binding capacity (dynamic adsorption amount) at 10% breakthrough was calculated by using the following formula.

$$q_{10} = c_f F (t_{10} - t_0)/V_B$$

$q_{10}$: dynamic binding capacity (mg/mL of wet resin) at 10% breakthrough
$c_f$: concentration (mg/mL) of BSA that has been injected in
F: flow rate (mL/min)
$V_B$: bed volume (mL)
$t_{10}$: time (min) at 10% breakthrough
$t_0$: BSA injection initiation time (min)

(Evaluation of Alkali Resistance)

The DEAE-modified separation material thus obtained was stirred for 24 hours in a 0.5 M aqueous solution of sodium hydroxide and washed with a phosphate buffer solution, and then the DEAE-modified separation material was packed under the conditions similar to those for the evaluation of column characteristics. The 10% breakthrough dynamic adsorption amount of BSA was measured and compared with the dynamic adsorption amount before the alkali treatment. The case in which the reduction ratio of the dynamic adsorption amount was 3% or less was rated as "A"; the case in which the reduction ratio was more than 3% and 20% or less was rated as "B"; and the case in which the reduction ratio was more than 20% was rated as "C". The results are presented in Table 3.

(Evaluation of Durability)

Water was caused to flow through a column at a flow rate of 800 cm/h, and the column pressure was measured. Subsequently, the flow rate was increased to 3,000 cm/h, and liquid permeation was carried out for 1 hour. When the column pressure was decreased to 800 cm/h again, the case in which the column pressure increased by 10% or more compared to the initial value (before the flow rate was increased to 3,000 cm/h) was rated as "B"; and the case in which the column pressure increased by less than 10% was rated as "A".

Example 2

Porous polymer particles 2 were synthesized in the same manner as in the synthesis of the porous polymer particles 1, except that the amount of use of SPAN 80 was changed to 8 g. The porous polymer particles 2 thus obtained were treated by a method similar to that for the porous polymer particles 1, and thereby a separation material and a DEAE-modified separation material were obtained. The separation material and the DEAE-modified separation material were evaluated in the same manner as in Example 1.

Example 3

Porous polymer particles 3 were synthesized in the same manner as in the synthesis of the porous polymer particles 1, except that the amount of use of SPAN 80 was changed to 9 g. The porous polymer particles 3 thus obtained were treated by a method similar to that for the porous polymer particles 1, and thereby a separation material and a DEAE-modified separation material were obtained. The separation material and the DEAE-modified separation material were evaluated in the same manner as in Example 1.

Example 4

Porous polymer particles 4 were synthesized in the same manner as in the synthesis of the porous polymer particles 1, except that divinylbenzene (16 g) was changed to divinylbenzene (14 g) and octanol (2 g). The porous polymer particles 4 thus obtained were treated by a method similar to that for the porous polymer particles 1, and thereby a separation material and a DEAE-modified separation material were obtained. The separation material and the DEAE-modified separation material were evaluated in the same manner as in Example 1.

Example 5

Porous polymer particles 5 were synthesized in the same manner as in the synthesis of the porous polymer particles 1, except that divinylbenzene (16 g) and SPAN 80 (6 g) were changed to divinylbenzene (14 g), octanol (5 g), and SPAN 80 (3 g). The porous polymer particles 5 thus obtained were treated by a method similar to that for the porous polymer particles 1, and thereby a separation material and a DEAE-modified separation material were obtained. The separation material and the DEAE-modified separation material were evaluated in the same manner as in Example 1.

Comparative Example 1

Porous polymer particles 6 were synthesized in the same manner as in the synthesis of the porous polymer particles 1, except that divinylbenzene (16 g) was changed to divinylbenzene (4 g) and dihydroxypropyl methacrylate (8 g). The porous polymer particles 6 thus obtained were DEAE-modified without forming a coating layer, and thereby a separation material was obtained. The separation material was evaluated in the same manner as in Example 1.

Comparative Example 2

Commercially available agarose particles (Capto DEAE; GE Healthcare Co.) as it were used as a separation material (porous polymer particles 7) without any change. The separation material was evaluated in the same manner as in Example 1.

Comparative Example 3

Porous polymer particles 8 were synthesized in the same manner as in the synthesis for the porous polymer particles 1, except that divinylbenzene (16 g) and SPAN 80 (6 g) were changed to 2,3-dihydroxypropyl methacrylate (11.2 g), ethylene glycol dimethacrylate (4.8 g) and SPAN 80 (5 g). The porous polymer particles 8 (4 g) after washing were added to 6 g of a solution prepared by dissolving 1 g of dextran (molecular weight 150,000), 0.6 g of sodium hydroxide, and 0.15 g of sodium borohydride in distilled water, and the solution was impregnated into the pores of the porous polymer particles 8. The dextran solution-impregnated polymer thus obtained was added to 1 L of a 1 mass % ethyl cellulose toluene solution and stirred, and the mixture was dispersed and suspended. 5 mL of epichlorohydrin was added to the suspension liquid thus obtained, and the mixture was heated to 50° C. The mixture was stirred for 6 hours at this temperature, and thereby the dextran impregnated in the pores of the porous polymer particles 8 was subjected to a crosslinking reaction. After completion of the reaction, the suspension liquid was filtered so as to separate a gel-like substance thus produced, and the gel-like substance was washed sequentially with toluene, ethanol, and distilled water. Thus, a separation material was obtained. The separation material was evaluated in the same manner as in Example 1.

TABLE 1

| Item | Average particle size (μm) | Particle size C.V. (%) |
|---|---|---|
| Porous polymer particles 1 | 91 | 12 |
| Porous polymer particles 2 | 93 | 8 |
| Porous polymer particles 3 | 101 | 7 |
| Porous polymer particles 4 | 89 | 10 |
| Porous polymer particles 5 | 91 | 11 |
| Porous polymer particles 7 | 92 | 34 |
| Porous polymer particles 8 | 98 | 38 |

TABLE 2

| Item | Mode diameter in pore size distribution (μm) | Rupture strength (mN) | Porosity (%) | Specific surface area (m²/g) | Coating amount (mg/g of particles) | Ion exchange capacity (mmol/ml) | Linear flow rate (cm/h) at 0.3 MPa |
|---|---|---|---|---|---|---|---|
| Example 1 | 0.3 | 50 or more | 45 | 52.3 | 214 | 0.45 | 1700 |
| Example 2 | 0.5 | 50 or more | 50 | 40.1 | 164 | 0.37 | 1530 |
| Example 3 | 0.5 | 12.5 | 62 | 50.1 | 205 | 0.41 | 1230 |
| Example 4 | 0.2 | 20 | 63 | 82.3 | 337 | 0.51 | 1100 |
| Example 5 | 0.15 | 41 | 65 | 95.1 | 389 | 0.63 | 1050 |
| Comparative Example 1 | 0.1 | 8 | 55 | 93.2 | — | 0.12 | 540 |
| Comparative Example 2 | 0.15 | 50 or more | 62 | 82.2 | — | 0.31 | 700 |
| Comparative Example 3 | 0.1 | 5 | 56 | 15.4 | — | 0.23 | 420 |

TABLE 3

| Item | Non-specific adsorption (mg/mL of particles) | Dynamic adsorption amount (mg/mL of particles) | Alkali resistance | Degree of hygroscopicity (%) | Durability |
|---|---|---|---|---|---|
| Example 1 | 1 mg or less | 53 | A | 7 | A |
| Example 2 | 1 mg or less | 58 | A | 5 | A |
| Example 3 | 1 mg or less | 42 | A | 8 | A |
| Example 4 | 1 mg or less | 40 | A | 9 | A |
| Example 5 | 1 mg or less | 36 | A | 10 | A |
| Comparative Example 1 | 5 mg | 15 | B | 52 | B |
| Comparative Example 2 | 1 mg or less | 20 | A | 140 | B |
| Comparative Example 3 | 3 mg | 12 | B | 51 | B |

As is obvious from Tables 1 to 3, it was found that in the DEAE-modified separation materials of Examples in which the rupture strength was adjusted to 10 mN or greater, the liquid permeation rate at 0.3 MPa was very fast, and non-specific adsorption to the particles was low in level. Furthermore, it was found that in the DEAE-modified separation materials of the Examples, the dynamic adsorption amount maintained a high value even at 800 cm/h. It was fond that in the DEAE-modified separation materials of the Examples, alkali resistance was improved, and the dynamic adsorption amount did not change significantly before and after an alkali treatment.

REFERENCE SIGNS LIST

1 . . . Column, 2 . . . Separation material, 10 . . . Separatory column.

The invention claimed is:
1. A separation material comprising:
porous polymer particles that comprise a styrene-based monomer as a monomer unit; and
a coating layer that comprises a crosslinked modified agarose and covers at least a portion of the surface of the porous polymer particles,
wherein the rupture strength is 10 mN or higher, and
the separation material comprises 164 to 389 mg of the coating layer per 1 g of the porous polymer particles.
2. The separation material according to claim 1, wherein the porosity is 40% to 70%.
3. The separation material according to claim 1, wherein the degree of hygroscopicity is 1% to 30% by mass.
4. The separation material according to claim 1, wherein the specific surface area is 30 m2/g or more.
5. The separation material according to claim 1, wherein the porous polymer particles comprise divinylbenzene as a monomer unit at a proportion of 50% by mass or more based on the total mass of the monomers.

6. The separation material according to claim 1, wherein the coefficient of variation of the particle size of the porous polymer particles is 3% to 15%.

7. The separation material according to claim 1, wherein the separation material is configured to be packed in a column and provide a liquid permeation rate of 800 cm/h or higher at the time when the column pressure is 0.3 MPa.

8. A separatory column comprising a column; and the separation material according to claim 1 that is packed in the column.

9. The separatory column according to claim 8, wherein a liquid permeation rate of 800 cm/h or higher at the time when the column pressure is 0.3 MPa.

\* \* \* \* \*